US008361782B2

(12) United States Patent
Pugia et al.

(10) Patent No.: US 8,361,782 B2
(45) Date of Patent: Jan. 29, 2013

(54) PIEZO DISPENSING OF A DIAGNOSTIC LIQUID INTO MICROFLUIDIC DEVICES

(75) Inventors: Michael J. Pugia, Granger, IN (US); James A. Profitt, Goshen, IN (US)

(73) Assignee: Siemens Healthcare Diagnostics, Inc., Tarrytown, NY (US)

( * ) Notice: Subject to any disclaimer, the term of this patent is extended or adjusted under 35 U.S.C. 154(b) by 394 days.

(21) Appl. No.: 12/598,141

(22) PCT Filed: Mar. 14, 2008

(86) PCT No.: PCT/US2008/056983
§ 371 (c)(1), (2), (4) Date: Oct. 29, 2009

(87) PCT Pub. No.: WO2008/137212
PCT Pub. Date: Nov. 13, 2008

(65) Prior Publication Data

US 2010/0093109 A1 Apr. 15, 2010

Related U.S. Application Data

(60) Provisional application No. 60/915,450, filed on May 2, 2007.

(51) Int. Cl.
*C12M 1/36* (2006.01)

(52) U.S. Cl. ................. 435/286.5; 435/297.4; 427/2.11; 427/2.12; 436/53

(58) Field of Classification Search ........................ None
See application file for complete search history.

(56) References Cited

U.S. PATENT DOCUMENTS

| | | | | |
|---|---|---|---|---|
| 4,849,340 | A | 7/1989 | Oberhardt | |
| 4,879,097 | A | 11/1989 | Whitehead et al. | |
| 5,063,396 | A | 11/1991 | Shiokawa et al. | |
| 5,209,904 | A | 5/1993 | Forney et al. | |
| 5,518,179 | A | 5/1996 | Humberstone et al. | |
| 6,083,763 | A | 7/2000 | Balch | |
| 6,355,487 | B2 | 3/2002 | Kowallis | |
| 6,394,363 | B1 | 5/2002 | Arnott et al. | |
| 6,485,918 | B1 | 11/2002 | Schermer et al. | |
| 6,656,432 | B1 | 12/2003 | Hirota et al. | |
| 6,833,111 | B2 | 12/2004 | Robertson et al. | |
| 8,263,414 | B2 | 9/2012 | Pugia et al. | |
| 2003/0132112 | A1 | 7/2003 | Beebe et al. | |
| 2004/0043421 | A1 | 3/2004 | Beumer et al. | |
| 2004/0147034 | A1 | 7/2004 | Gore et al. | |
| 2004/0203136 | A1* | 10/2004 | Kellogg et al. | 435/287.2 |
| 2004/0265172 | A1 | 12/2004 | Pugia et al. | |

(Continued)

FOREIGN PATENT DOCUMENTS

| | | | |
|---|---|---|---|
| EP | 0353591 | A2 | 2/1990 |
| EP | 1004870 | A1 | 5/2000 |

(Continued)

OTHER PUBLICATIONS

PCT/US2008/056983; PCT International Search Report and Written Opinion dated Aug. 14, 2008.

(Continued)

*Primary Examiner* — N. C. Yang
(74) *Attorney, Agent, or Firm* — Noam R. Pollack

(57) ABSTRACT

Assays in which samples of biological fluids are dispensed into the inlet port of a microfluidic device are improved in the accuracy and repeatability by dispensing the biological sample and/or associated liquids in small droplets and at timed intervals to control the operation of the microfluidic device.

19 Claims, 1 Drawing Sheet

U.S. PATENT DOCUMENTS

| | | | | |
|---|---|---|---|---|
| 2006/0039829 | A1 | 2/2006 | Suk et al. | |
| 2010/0167416 | A1* | 7/2010 | Kabilan et al. | 436/501 |

FOREIGN PATENT DOCUMENTS

| | | | |
|---|---|---|---|
| EP | 1480750 | | 1/2004 |
| JP | 2004521315 | | 7/2004 |
| JP | 2007520693 | | 7/2007 |
| JP | 2008542715 | | 11/2008 |
| WO | 9222800 | A1 | 12/1992 |
| WO | 0035590 | A1 | 6/2000 |
| WO | 0207884 | A2 | 1/2002 |
| WO | 03072258 | A1 | 9/2003 |
| WO | 2005003724 | A2 | 1/2005 |
| WO | 2005033713 | A1 | 4/2005 |
| WO | 2006042734 | | 4/2006 |
| WO | 2006042838 | A1 | 4/2006 |
| WO | 2006043181 | A2 | 4/2006 |
| WO | 2006127631 | A1 | 11/2006 |

OTHER PUBLICATIONS

Notification of Reasons for Rejection of corresponding Japanese Patent Application No. 2010-506358 issued on Aug. 28, 2012.

* cited by examiner

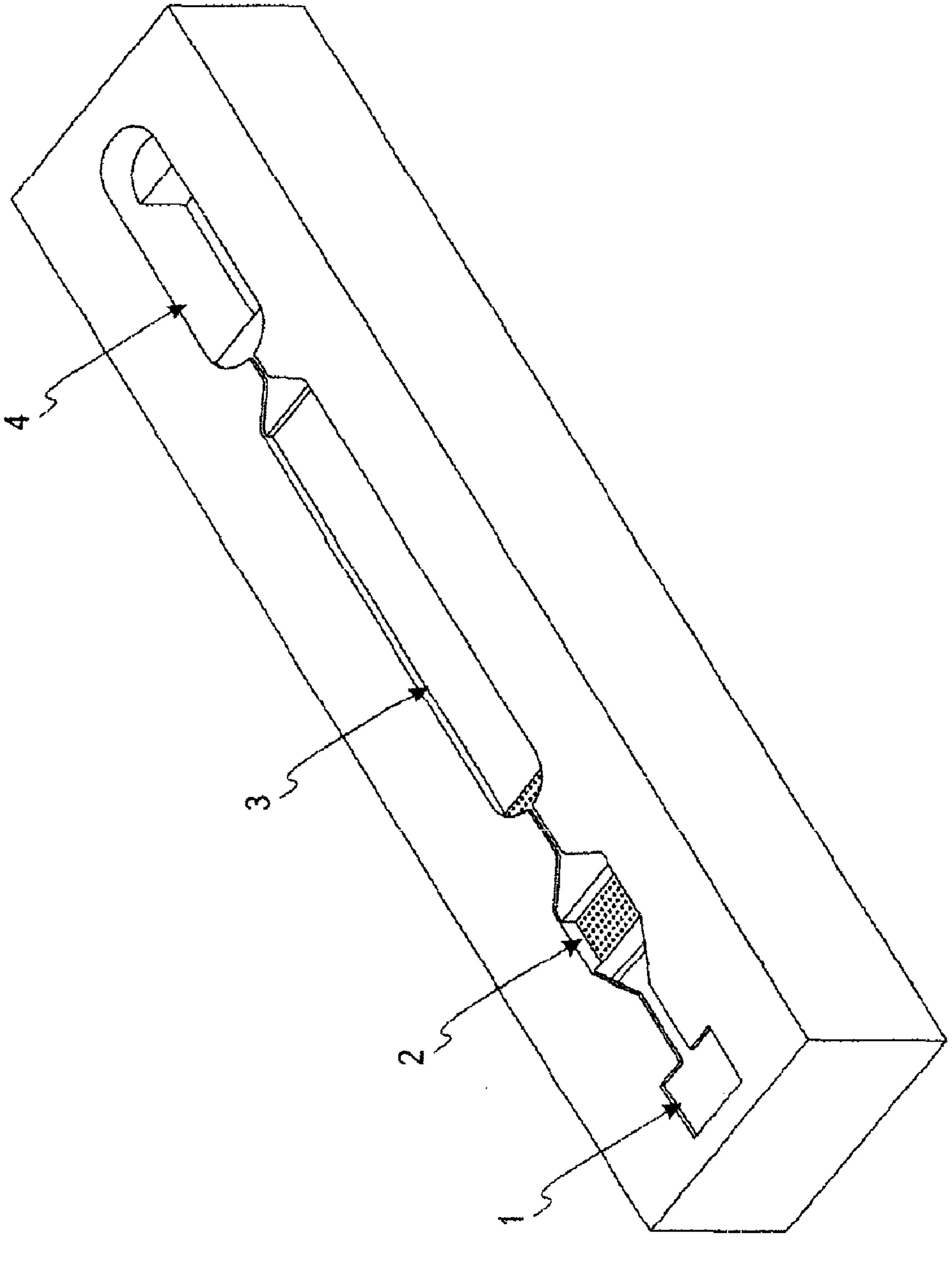
4
3
2
1

PIEZO DISPENSING OF A DIAGNOSTIC LIQUID INTO MICROFLUIDIC DEVICES

FIELD OF THE INVENTION

This invention relates to reagents and instruments used to measure the quantity of analytes in biological samples by the reaction of the analytes with reagents to produce a detectable response.

BACKGROUND OF THE INVENTION

Depositing Liquids on Reagent-Containing Substrates

Many instruments have been developed to measure the quantity of analytes in biological samples, for example urine, blood, salvia, or extracts of mucus or tissue. Typically, a sample liquid is applied to a surface containing reagents that react with the analyte. The reagents produce a detectable response that is measured and related to the amount of the analyte. The surface usually will be either hydrophilic or hydrophobic in nature, e.g. filter paper compared to polystyrene. Some devices use combinations of surfaces, such as urinalysis strip tests that use hydrophilic filter paper pads on top of a hydrophobic polystyrene handle. In the typical test, a strip containing unreacted reagents is dipped, i.e. fully immersed in a liquid sample, and the reaction between the analyte in the sample and the reagents is measured, usually by optical methods. The unreacted reagents themselves may be water soluble or insoluble. They are deposited or immobilized and dried in a porous substrate. The substrate is attached or placed onto the supporting surface. Additionally, a liquid with or without reagents can be used during an assay. The liquid reagents can be applied to the surfaces of substrates already containing dried reagents, before, after or during the reaction with the analyte, typically being added after a sample has been applied. The volume of samples and reagents should be as small as possible for obvious reasons relating to cost and convenience. What is less obvious is that it is often difficult to obtain a uniform and accurate response when applying small amounts of liquid reagents or biological samples to surfaces containing reagents. The response of the analyte with reagents is smaller than the reaction area in smaller and less analyte is present.

The substrate can be used to amplify the reaction response. Thin films, e.g. membranes, can be immobilized with affinity reagents to allow capturing and concentration of reactants in read zones. Directing flow of liquids in a desired direction, e.g. laterally rather than vertically, can increase efficiency by increasing the number of fluidic exchanges between the liquid sample or reagent and the reaction zone. Each exchange allows further reaction of the analyte to occur, thereby amplifying the signal. Modification of the surface of the substrate allows reagents to be isolated in the reaction zone. Further, the nature of the surface itself can be used to increase the reactivity of the analyte, for example by increasing solubilization of reagents or to favor reactions with reagents on the surface.

Most biological samples and liquid reagents will have a significant water content and thus will be compatible with hydrophilic substrates and incompatible with hydrophobic surfaces. The sample and reagent liquids when dispensed spread rapidly across hydrophilic substrates and are repelled by hydrophobic substrates. The contact between the dispensed liquid and the reagents on the surface is made by direct dispensing onto the reacted or partially reacted area. However, when substrates are relatively hydrophobic, the dispensed liquid will form beads on the surface of the substrate that attempt to minimize their contact with the surface and therefore they do not spread uniformly over the reagent. Another difficulty associated with dispensing liquids is that the dried reagents may be either water soluble or water insoluble in nature. The insoluble dry reagents may not be readily accessible to the liquid samples, or soluble reagents may be dissolved and move with the liquid on the substrate. The reagents ideally should contact the sample uniformly, since the measurable response of the reagents to the sample, e.g. color development, should be uniform in order to obtain an accurate reading of the quantity of the analyte in the sample.

Another problem related to obtaining good contact between a dispensed liquid and a reagent on a surface is related to the physical nature of the samples. They vary in their physical properties such as surface tension, viscosity, total solids content, particle size and adhesion. Therefore, they are not easily deposited in consistent volumes uniformly over the reagent-covered substrate. Also, as the amount of the liquid sample is reduced, it becomes increasingly difficult to apply a consistent amount of a sample having varying properties to the reagents. In contrast, ink jet printing and the like rely on liquids developed for such uses and having consistent physical properties.

Deposition of droplets of liquid is a familiar operation. Examples include the ink jet-printer, either piezoelectric or bubble actuated, which forms print from the controlled deposition of multiple small droplets of about 2 to 300 μm diameter (typically 50 μm) containing from a few femtoliters to tens of nanoliters. Other methods of depositing small droplets have been proposed, which generally employ piezoelectric principles to create droplets, although they differ from typical ink jet printers. Examples are found in U.S. Pat. Nos. 5,063,396; 5,518,179; 6,394,363; and 6,656,432. Deposition of larger droplets (3-100 μl) through a syringe type pipette is known to be reproducible in diagnostic systems. This corresponds to single droplet diameters of about 2 to 6 mm. A commercial example of such pipette systems is the CLINITEK ALTAS® urinalysis analyzer. The droplet size can be greater or less than the nozzle size depending on the nozzle shape, pump type and pressures applied.

The problems discussed above are particularly observed when a liquid sample is dispensed as droplets onto a reagent-containing pad. It has been found that the interactions of the pad's surface and the reagents were creating inaccurate responses when the sample was added as a droplet, rather than completely covering the reagent pad by immersing the reagent pad (dipping it) into the sample liquid, as is frequently done. Large droplets on the order of 3 to 100 μL do not transfer into the reagent when the substrate is too hydrophobic and form a bubble on the surface. They overwhelm the reagent with excess fluid if the surface is hydrophilic. Smaller droplets, of a few femtoliters to tens of nanoliters, can also be a problem when deposited on a substrate that is too hydrophobic as they lack the volume to completely cover the surface area and will randomly aggregate in non-uniform patterns. Small drops also allow open spaces for migration of water-soluble reagents. These tiny droplets are also prone to evaporation of liquids and to formation of aerosols, which are considered to be biohazardous if comprised of urine or blood specimens. Thus, if a liquid is to be deposited as droplets on test pads, rather than dipping the pads in the sample, improvements were needed.

After contact between dispensed liquids and reagents is complete, the results may be read using one of several methods. Optical methods are commonly used, which rely on spectroscopic signals to produce responses. Results must be reproducible to be useful. Optical measurements are affected by the reagent area viewed and by the time allowed for the dispensed liquids and reagents to react. Formation of non-uniform areas within the field of view and changes in the amount of reaction time cause increased errors. For example, a measurement made of a sample or reagent which has spread non-uniformly across the substrate gives a different result each time it is read.

In co-pending U.S. patent application Ser. No. 11/135,928, published as U.S. 2006/0263902 A1, commonly assigned with this application, the inventors reported their methods of depositing biological fluids and reagents as fine droplets onto reagent-carrying substrates. They demonstrated that the reagent-carrying substrates behaved differently, depending on the water solubility of the reagents and the surface energy of the substrate, that is, whether the reagent-carrying substrates were hydrophilic or hydrophobic. Depositing large droplets, e.g. 1.7-20.4 μL, was shown to provide less accurate results than when small droplets of about 50 pL to 1 μL were deposited on reagent-carrying surfaces. The inventors also found that small droplets were absorbed by the hydrophobic substrates, while large droplets were not readily absorbed.

Water soluble reagents were shown to dissolve and move with a liquid as it spreads on a reagent-carrying surface. The inventors found that that non-uniform reagent response which such movement caused would be moderated by depositing small droplets.

Depositing of small droplets was done either by nozzles having many small openings or by single nozzles, which could be moved relative to the reagent-carrying substrate, or vice versa, to cover the desired area. The reaction of liquid samples with reagents on the substrate could be read as an average of the area covered by the sample or preferably by scanning the reaction area one spot at a time and averaging the results.

Deposition Liquids into Microfluidic Devices

Adding biological samples and associated liquids to microfluidic devices used for analysis of biological samples may be done with various techniques. Very small samples of blood, urine and the like are introduced into such devices, where they come into contact with reagents capable of indicating the presence and quantity of analytes found in the sample.

Problems associated with depositing biological samples and other liquids that may be needed for analyzing the samples have been discussed in U.S. patent application Ser. No. 10/608,671, published as U.S. 2004/0265172 A1. Particularly important requirements are the removal of air from the device as liquids are introduced and metering the amount of sample to be analyzed, and associated liquids, e.g. reagents, buffers, diluents and the like.

It has been found that, even after the problems just discussed have been overcome by proper design of the microfluidic device, measuring the amount of an analyte in a biological sample may not give the repeatability that one would like. In part, the problem relates to the variability inherent in these designs. First, the variability in the surface coating can cause liquids to creep over capillary stops or around reagent areas. This causes variations in the timing of liquid movements and the volumes reacted. Second, less experienced users can apply incorrect amounts of samples or reagents. Third, the internal dimensions of these microfluidic devices can differ from one chip to another when they are made in large quantities by low cost methods. The present inventors have found that such problems can be overcome, making significant improvements in the accuracy and repeatability of results.

SUMMARY OF THE INVENTION

The invention in one aspect is an improved method of assaying for the amount of an analyte contained in a biological fluid. The method comprises dispensing of samples of a biological fluid and/or associated liquids in droplets having diameters in the range of 0.05 to 1 mm into the inlet port of a microfluidic device. The dispensing of the biological sample and/or associated liquids is done at predetermined times to control the operation of the microfluidic device. The associated liquids are deposited as groups of droplets separated by intervals when no liquid is dispensed, thereby moving the sample into the desired position in the microfluidic device at times selected to optimize the assay.

BRIEF DESCRIPTION OF THE DRAWINGS

FIG. 1 shows the microfluidic device of Example 1.

DESCRIPTION OF THE PREFERRED EMBODIMENTS

Definitions

The following terms used herein are defined as follows:

"Spectroscopic image" refers to a detailed view of the optical response of a reagent-containing area to a biological sample deposited on the reagent-containing area, for example using a change in color, reflectance, transmission or absorbance or others such as Raman, fluorescence, chemiluminescence, phosphorescence, or electrochemical impedance spectroscopy, which enables examination of sub-units of the entire reagent-containing area. The image can be multi-dimensional with position(i.e. x-y) being added to the optical response.

"Hydrophilic" surfaces are those that have a less than 90° contact angle between the surface and a drop of water placed thereon.

"Hydrophobic" surfaces are those that have a 90° or larger contact angle between the surface and a drop of water placed thereon.

Interaction of Liquids with Porous Substrate

The present invention provides improved control of reactions occurring within porous substrates ("pads"), which contain dried reagents and are located within microfluidic devices. The reactions result from the interaction between a sample liquid and a reagent-containing pad.

When a liquid sample containing an unknown amount of an analyte contacts a reagent-containing pad, the liquid must dissolve the reagent so that the reaction with the analyte can occur, which produces a detectable result e.g. a distinctive optical signal, such as color, which is detected by spectrographic means. The speed at which the reaction occurs and the extent to which the result is detectable is affected by a number of factors. Such factors include the accessibility of the reagent, its solubility in the liquid, and the relative amounts of the reagent and the liquid in the region in which the liquid is placed. The uniform application of liquids to a porous pad is important if consistent and accurate results are to be obtained. Likewise, the characteristics of the pad, e.g. its hydrophobicity/hydrophilicity, its porosity and capillarity, and its thickness are also factors which determine the assay's results. The pad characteristics not only affect the volume of liquid absorbed, but also the solubilizing and surface interactions of reagents dried onto the pad. They also affect the direction in which liquids flow and the ability to fix reagents in a specific location. For example, pads are often used with the films such as membranes that allow liquids to flow laterally rather than vertically. Thus the number of fluid exchanges that can be done in a defined reaction zone. When the reaction zones contain immobilized bioaffinity molecules, e.g. antibodies and nucleic acids, the capture efficiency is increased by the number of fluid exchanges. In practice, one skilled in the art finds that the physical characteristics of the pad itself, the reagents, and the sample liquid all must be considered in designing a useful assay system.

In contrast to direct deposition of a sample (and associated liquids) to a reagent-containing pad, in microfluidic devices the sample will be added to an inlet port and then transferred through intervening wells and capillary passageways to a chamber containing a reagent-containing pad. Often a sample is mixed or diluted with another liquid, such as a liquid reagent. The sample can be added to the microfluidic device before, at the same time as the liquid reagent, or after. Single or multiple inlet ports can be used. Although the sample, liquid reagent, and mixtures can flow differently, it is still important to distribute the liquids uniformly.

In the present invention, the timed application of sample liquids and/or other associated liquids in precise patterns in small increments at specific times into target areas, provides improved control of the interaction of the liquids with the reagent-containing pad to provide increased accuracy and uniformity of results.

Depositing Liquid Samples

In many assays, reagents are placed in porous substrates or "pads" and the substrates in strip form are dipped into the biological fluid being tested. Although such assays are useful, they are not necessarily as accurate or repeatable as desired. It was previously shown that depositing large sample droplets (i.e. 1-7 μL to 20.4 μL) was not as satisfactory as dipping strips in liquid. However, small droplets (i.e. 50 pL to 1 μL) provided superior results in an array of biological assays.

Two types of dispensing nozzles have been previously described. In the first, a single nozzle is used to dispense a sequence of single droplets onto the reagent-containing substrate. Either the nozzle or the substrate would be moved to provide uniform coverage in the desired area. The second type of nozzle used a plate drilled with a series of holes so that multiple sequences of droplets could be dispensed at one time. In either type, the smallest droplet size was considered to about 50 pL, which would be associated with hole diameters of about 45-50 μm. The nozzles could be operated by pressure from various sources. Using piezo actuators was one preferred method of dispensing the small droplets.

Microfluidic Devices

U.S. patent application Ser. No. 10/608,671, published as U.S. 2004/0265172 A1, discusses the entry and movement of biological samples into contact with reagents contained in microfluidic devices. Such devices typically have a total volume of about 0.1 to 200 μL, however, they may have large or smaller volumes depending on their use. In general, microfluidic devices can be operated by moving a first liquid with a predetermined amount of a second liquid, either to a capillary stop or to introduce a needed amount of the second liquid. The method of the invention provides more accurate movement of liquids in the microfluidic device.

Published application U.S. 2006/0263902 A1 describes the advantages of depositing small droplets of biological samples directly onto reagent-containing porous substrates. This method is not suited to microfluidic devices, which use capillary forces to move liquid samples into contact with reagents inside the microfluidic device.

Experience with microfluidic devices has shown that the results of assays are affected by the amount of the biological sample that reacts with the reagents. This is to be expected since the interpretation of the results, e.g. determining the amount of analyte from the color developed, is based on the amount of the analyte in the biological samples used to calibrate the measuring instrument. While the amount of the biological sample can be defined by using a well or capillary having a known volume, it has been found that the variation among groups of these small devices are sufficient to cause undesirable variability in results. Volume differences are one factor, but a factor of particular importance relates to the performance of what have been referred to as "capillary stops". These are places within the device where changes in the size of the capillary passageways are used to stop liquids from continuing to flow under capillary forces. In practice, biological samples and liquids such as buffers, wash liquids, additional reagents and the like may be added in amounts which cause capillary stops to be overcome, thus moving liquids forward in the device. For example, if a biological sample has been introduced into a microfluidic device and moved by capillary force to the entrance of a chamber containing reagents, where it pauses at a capillary stop, then the stop must be overcome in order to move the sample into the chamber. This may be done by introducing a liquid, e.g. a wash liquid, into the inlet port, which causes the capillary stop to be overcome and the biological sample to be moved into the reagent-containing chamber. The variation of the strength of the capillary forces and the capillary stops has been found to have an adverse impact on the performance of the microfluidic devices. While the devices provide useful information despite the variability, improvement was sought.

It was found that applying biological samples and other liquids to the inlet port of microfluidic devices in small droplets provided a significant advantage in controlling liquid movement through such devices. The capillary passages within microfluidic devices contain very small liquid volumes, e.g. 5 nL/mm. Thus, only small increments of liquids are used to overcome the capillary stops. Exact dispensing of liquid droplets is needed to trigger capillary stops, with the starting and stopping of the dispensing being controlled within nanoseconds. This accurate dispensing is done at times determined by the reaction of reagents, as measured by spectroscopic means. The pattern of dispensing events has been found to be important in maintaining uniform flow. In particular, it was found that dispensing liquids in known amounts, separated by intervals in which no liquid was dispensed made it possible to control the sequence of liquid movements in a manner that was not previously attainable. This is illustrated in the following example in which a biological sample, (whole blood) was added to a microfluidic device, followed by lysis and wash solutions.

EXAMPLE 1

The following abbreviations are used:

PBS—Phosphate Buffered Saline

BSA—Bovine Serum Albumin

FITC—fluorescein isothiocyanate

An $HbA_{1C}$ immunoassay was carried out on a nitrocellulose substrate (5.0 μm pore), on which was placed two 4 mm wide capture bands. The first band contained an $HbA_{1C}$ agglutinator (a mimic of the analyte $HbA_{1C}$; 1 mg/mL in PBS, pH 7.4). The second band contained a monoclonal anti-FITC antibody (3 mg/mL in 0.05 borate, pH 8.5).

A conjugate for binding the $HbA_{1C}$ analyte was made which contained blue latex particles attached to BSA labeled with FITC and $HbA_{1C}$ antibody. Two concentrations were prepared for use in high (8-15% $HbA_{1C}$) and low (3-8% $HbA_{1C}$) concentration assays. The BSA-labeled material was attached to blue latex particles (300 nm, 67 μeq. of COOH/g) at a loading of 30 μg BSA-FITC-anti-$HbA_{1C}$ per mg of latex. A wash solution of PBS containing 01% BSA was used for the high range and for the low range a 1:10 dilution of anti-FITC antibody latex conjugate. The anti-FITC antibody was prepared with 10 μg antibody per 1 mg. of blue latex particles. The conjugate was dried into glass fiber paper diluted with casein blocking buffer. For the high range the conjugate was diluted in a 1:4 ratio, for the low range a 1:400 dilution was used. When the $HbA_{1C}$ was present in a biological sample, in this case blood, it would bind to the conjugate. Then the bound conjugate would not bind to the agglutination band, but would pass to the second band where it would be bound to the anti-FITC antibody. Excess conjugate would be bound by the first band since it would bind to the $HbA_{1C}$ antibody in the conjugate. By measuring the relative amounts of FITC found on the two capture bands, the amount of $HbA_{1C}$ in the sample could be determined.

The nitrocellulose strip containing the two capture bands was placed in a microfluidic device, illustrated in FIG. 1. This device has four chambers connected by capillary channels and has a total volume of about 20 μL. The first chamber is the inlet port for the device. It is open to the surroundings. Chamber 2 contains the conjugate on a glass fiber paper and supported on microposts. The nitrocellulose capture strip is in Chamber 3, the entrance of which contains an array of microposts to distribute the liquids. Chamber 4 contains a porous pad used to remove excess liquid from Chamber 3.

In use, the sample (whole blood) was added to Chamber 1 which determine the volume of the sample. It flows through a capillary and is stopped at the entrance to Chamber 2. A lysis solution (Cellytic-M, Sigma Aldrich, St. Louis, Mo.) was added to force the sample into Chamber 2, where it contacts the conjugate. After the conjugate particles have reacted with the sample, wash liquid was added to Chamber 1 to force the sample and the conjugate through the stop at the entrance of Chamber 3, so that the diluted sample passes over the capture bands on the strip. Color is developed from FITC in the capture bands and read with a CCD camera as the optical detector and then compared by appropriate software with calibration data. Additional liquid is fed into Chamber 1 to move the residual sample into Chamber 4, which contains an absorbent pad.

Tests were carried out with this microfluidic device in which three methods were used to add liquids to Chamber 1. A conventional capillary pipette having an opening of about 0.3 to 2 mm and which dispensed droplets of about 0.3-100 μL, depending on the fill length, was used to place the sample and other liquids in the inlet port. A micro-dispensing head having an opening of about 50 μm dispensed the sample and liquids in a continuous manner without pause. The same micro-dispensing head also was used intermittently, with intervals in which no liquids were dispensed, and timed to move precisely to overcome the capillary stops. It was found that dispensing small droplets at times most appropriate for the reactions give clearly superior results, as is shown in the following table.

| Dispensing Method | % Over fills | % Under fills | % non-uniform color | Timing of Response |
|---|---|---|---|---|
| Large pipette | 32% | 23% | 18% | 10-20 sec |
| Micro-dispensing (continuous) | 16% | 9% | 17% | ~3-6 sec |
| Micro-dispensing in timed groups | 0.1% | 0.3% | 1.2% | ~>0.01 sec |

In the table above, "% overfill or % underfill" refers to a series of tests in which the microfluidic device of FIG. 1 was tested and in which it was found that more or less liquid was added than was required for the reaction. "% non-uniform color" refers to the color developed in Chamber 3, which indicates the amount of the conjugate captured and permits calculation of the amount of $HbA_{1C}$ in the sample. "Timing of response" refers to the minimum time found from experience for liquid to begin flowing from Chamber 2 to Chamber 3 in the microfluidic device. These assays typically are performed within 1 to 10 minutes, including both incubation and color development. Errors in incubation and color development times lead to errors in response since more or less reagent is reacted than expected.

EXAMPLE 2

The microdispensing head used in the previous example was capable of dispensing droplets of about 100 pL at a rate of 85 drops/millisecond. In addition to dispensing periods separated by intervals when no liquid was dispensed, it was possible to control the volume dispensed in each period, that is the number of droplets in each period. This ability made it possible to more accurately control the movement of the sample and diluents through the microfluidic device. In the $HbA_{1C}$ assay described above it was important to provide the proper time for incubation of the sample with the conjugate and the reaction of the sample/conjugate to be completed before washing the assay strip. This requires monitoring of the progress of the sample and controlling the timing of the addition of diluents. It is important to optimizing the assay that the sample and the sample/conjugate be moved at certain speeds. This is possible when the position of the sample and sample/conjugate are continually monitored by and the addition of diluents is controlled accordingly.

In this example the microdispensing was controlled to provide groups of 85 droplets per millisecond with intervals of 0.1 sec. When compared with the pipette and continuous microdispensing the following results were obtained.

| Dispensing Method | Timing Accuracy | Smallest Volume Added | Volume Tolerance |
|---|---|---|---|
| Large Pipette | ~1 seconds | 1.7 μL | 0% |
| Microdispensing (continuous) | ~0.5 milliseconds | 5.0 nL | 80% |
| Microdispensing Intensified Groups | ~0.01 milliseconds | 100 pL | 99.6% |

In the above table, "Timing Accuracy" refers to the minimum period of time required to operate the dispensing method. "Smallest Volume Added" refers to the extent to which each dispensing method can be controlled. "Volume Tolerance: refers to the variation in volume from that desired for optimum operation of the microfluidic device. In this example, the capillaries between chambers have a volume of about 50 nL which is the smallest volume that can be added before the capillary stop at the end of the capillary is triggered. The volume tolerance is zero for the large pipette when the smallest volume dispensed is more than 50 nL. Even when using a capillary as a pipette, a volume of 0.3 μL (300 nL) would still have a zero volume tolerance.

Using microdispensing with intensified groups of droplets, the smallest group is one drop. In this example as the drop is dispensed at 85 drops/msec and each drop has a volume of 100 pL. The volume then is about 0.1 μL/msec (8.5 nL/msec). This is generally a good operating range. It provides a high volume tolerance and the microfluidic device is reliably fired 99.996% of time. As the device is monitored by a spectrographic image, a miss-fire or variation in the microfluidic capillary volume can be corrected for by an additional group of droplets. The typical operating range is 30 to 150 drops/msec and the drop volumes are from about 30 pL to 1000 nL.

When using continuous micro-dispensing, the dispenser can be stopped electronically, but more drops than one are typically dispensed. In this example "Smallest volume added" would be 50 drops of 0.100 nL or 5 nL. This means the volume tolerance is not as high for the device or 80% of time (4 out of 5). Since microfluidic device can operate with capillaries only holding 5 nL, this tolerance is less acceptable than that observed for microdispensing with intensified groups.

What is claimed is:

1. A method of assaying in a microfluidic device the amount of an analyte in a biological fluid, said microfluidic device having at least one sample inlet port, at least one air vent, and at least one reagent-containing chamber, comprising:

(a) dispensing a sample of said biological fluid into said at least one sample inlet port of said microfluidic device, said sample moving by capillary force to a capillary stop through a capillary passageway communicating with said at least one sample inlet;

(b) dispensing into said at least one inlet port of (a) a portion of a liquid different from said sample of (a), said liquid portion being sufficient to force said sample past said capillary stop, said liquid portion being dispensed in the form of a group of droplets having diameters in the range of 0.05 to 1 mm, said groups of droplets being separated by intervals when no droplets are dispensed, said liquid portion being added at a predetermined time after introducing said sample.

2. A method of claim 1 wherein said different liquid of (b) is introduced in an amount sufficient to displace all of said sample of (a) to a position in said microfluidic device beyond said capillary stop.

3. A method of claim 2 wherein said displaced sample of claim 2 contacts a reagent dispensed in said at least one reagent-containing chamber and displaces air found in said at least one chamber.

4. A method of claim 3 wherein said sample and said reagent react and produce a detectable result related to the amount of said analyte in said sample.

5. A method of claim 2 wherein said displaced sample contacts a conditioning agent or a carrier agent to prepare said sample for subsequent contact with a reagent.

6. A method of claim 1 wherein said groups of droplets of said different liquid of (b) are dispensed by a micro-dispensing nozzle at a rate of about 30 to 150 thousand drops per second.

7. A method of claim 1 wherein said microfluidic device has a total volume of about 0.1 to 200 μL.

8. A method of claim 1 wherein the smallest group of droplets have a volume of about 100 pL.

9. In a method of assaying in a microfluidic device the amount of an analyte in a biological fluid, said microfluidic device having at least one sample inlet port, at least one air vent, and at least one reagent-containing chamber, said assay comprising dispensing a sample of said biological fluid into said at least one inlet port and displacing said sample by dispensing a liquid different from said sample into said at least one inlet port, the improvement comprising dispensing said different liquid in the form of group of droplets having diameters in the range of 0.05 to 1 mm, said groups of droplets being separated by intervals when no droplets are dispensed.

10. A method of claim 9 wherein said sample of biological fluid moves by capillary force to a capillary stop in a capillary passageway communicating with said at least one sample inlet and said different liquid is dispensed in an amount sufficient to force said sample past said capillary stop.

11. A method of claim 10 wherein said sample of biological fluid is forced past said capillary stop into said at least one reagent-containing chamber.

12. A method of claim 10 wherein said sample and said reagent react and produce a detectable result related to the amount of said analyte in said sample.

13. A method of claim 10 wherein said sample contacts a conditioning agent or a carrier agent to prepare said sample for subsequent contact with a reagent.

14. A method of claim 9 wherein said groups of droplets of said different liquid are dispensed by a micro-dispensing nozzle at a rate of about 30 to 150 thousand drops per second.

15. A method of claim 9 wherein said microfluidic device has a total volume of about 0.1 to 200 μL.

16. A method of claim 9 wherein the smallest group of droplets has a volume of about 100 pL.

17. A method of claim 10 wherein the volume of different liquid dispensed is about 5nL.

18. A method of operating a microfluidic device, said microfluidic device having at least one inlet port, at least one air vent, and at least one chamber, comprising:

(a) dispensing into said at least one inlet port a predetermined amount of a first liquid in the form of groups of droplets having diameters in the range of 0.05 to 1 mm;

(b) dispensing into said at least one inlet port a predetermined amount of a second liquid sufficient to force said first liquid from said at least one inlet port, said second liquid being dispensed in the form of a group of droplets having diameters in the range of 0.05 to 1 mm, said groups of droplets being separated by intervals when no droplets are dispensed, said second liquid being added at a predetermined time after introducing said first liquid.

19. A method of claim 18 wherein said microfluidic device comprises a capillary passageway communicating between said at least one inlet port, and said at least one chamber, said first liquid moving by capillary force from said inlet port to a capillary stop at the entrance to said at least one chamber.

* * * * *